United States Patent
Swords (10) Patent No.: US 7,655,047 B2
(45) Date of Patent: Feb. 2, 2010

(54) CRANIOFACIAL IMPLANT

(75) Inventor: Greg Swords, Atlanta, GA (US)

(73) Assignee: Porex Surgical, Inc., Newnan, GA (US)

( * ) Notice: Subject to any disclaimer, the term of this patent is extended or adjusted under 35 U.S.C. 154(b) by 147 days.

(21) Appl. No.: 10/517,843

(22) PCT Filed: Apr. 16, 2004

(86) PCT No.: PCT/US2004/011903

§ 371 (c)(1), (2), (4) Date: Jul. 12, 2005

(87) PCT Pub. No.: WO2004/093743

PCT Pub. Date: Nov. 4, 2004

(65) Prior Publication Data

US 2005/0288790 A1     Dec. 29, 2005

Related U.S. Application Data (60) Provisional application No. 60/463,036, filed on Apr. 16, 2003, provisional application No. 60/496,684, filed on Aug. 21, 2003.

(51) Int. Cl.
*A61F 2/02* (2006.01)

(52) U.S. Cl. ............... 623/17.18; 623/17.19; 623/23.54; 623/23.55

(58) Field of Classification Search ... 623/17.17–17.19, 623/23.5, 23.52–23.55, 23.58, 23.76; 606/151, 606/215, 213
See application file for complete search history.

(56) References Cited

U.S. PATENT DOCUMENTS

| | | | |
|---|---|---|---|
| 4,089,071 A | 5/1978 | Kalnberz et al. | |
| 4,164,794 A | 8/1979 | Spector | |
| 4,479,271 A | 10/1984 | Bolesky | |
| 4,502,161 A | 3/1985 | Wall | |
| 4,531,916 A * | 7/1985 | Scantlebury et al. | ........ 433/173 |
| 4,693,721 A | 9/1987 | Ducheyne | |
| 4,756,862 A | 7/1988 | Spector | |
| 4,863,474 A | 9/1989 | Brown et al. | |

(Continued)

FOREIGN PATENT DOCUMENTS

CN     1225373     11/1999

(Continued)

OTHER PUBLICATIONS

Helfen, et al., 'Zementfreie Pfanne und zementierter Schaft-Konzept einger „Hybrid-Lösung sowie Ergebnisse einer drei- bis sechsjährigen klinischen Erfahrung,' Z. Ortho., 131:578-584 (1993), Abstr.

(Continued)

*Primary Examiner*—David Isabella
*Assistant Examiner*—Suba Ganesan
(74) *Attorney, Agent, or Firm*—Kilpatrick Stockton LLP (57) ABSTRACT

A composite surgical implant that is made of a planar sheet of a thermoplastic resin that includes a top surface (400), a bottom surface (410), and a surgical grade metal mesh (405) contained therein. The implant may be bent by hand, wherein upon the displacement of the implant, the implant will generally maintain the shape to which it has been displaced.

12 Claims, 7 Drawing Sheets

U.S. PATENT DOCUMENTS

| | | | |
|---|---|---|---|
| 4,976,738 A | 12/1990 | Frey et al. | |
| 4,978,355 A | 12/1990 | Frey | |
| 5,030,233 A | 7/1991 | Ducheyne | |
| 5,139,497 A | 8/1992 | Tighman et al. | |
| 5,250,048 A | 10/1993 | Gundolf | |
| 5,282,861 A | 2/1994 | Kaplan | |
| 5,290,315 A | 3/1994 | DeCarlo | |
| 5,346,492 A | 9/1994 | Morgan | |
| 5,372,598 A | 12/1994 | Luhr | |
| 5,380,328 A | 1/1995 | Morgan | |
| 5,383,931 A | 1/1995 | Hehli et al. | |
| 5,433,996 A | 7/1995 | Kranzler | |
| 5,443,512 A | 8/1995 | Parr | |
| 5,443,519 A | 8/1995 | Averill | |
| 5,456,723 A | 10/1995 | Steinemann | |
| 5,468,242 A | 11/1995 | Reisberg | |
| 5,489,305 A | 2/1996 | Morgan | |
| 5,496,372 A | 3/1996 | Hamamoto et al. | |
| 5,545,226 A | 8/1996 | Wingo | |
| 5,669,909 A | 9/1997 | Zdeblick | |
| 5,690,631 A | 11/1997 | Duncan et al. | |
| 5,743,913 A | 4/1998 | Wellisz | |
| 5,755,809 A | 5/1998 | Cohen | |
| 5,766,176 A | 6/1998 | Duncan | |
| 5,769,637 A | 6/1998 | Morgan | |
| 5,814,048 A | 9/1998 | Morgan | |
| 5,824,088 A | 10/1998 | Kirsch | |
| 5,980,540 A | 11/1999 | Bruce | |
| 5,989,427 A | 11/1999 | Ellard et al. | |
| 5,989,472 A | 11/1999 | Ashby et al. | |
| 6,031,148 A * | 2/2000 | Hayes et al. | 623/11.11 |
| 6,065,197 A | 5/2000 | Iseki et al. | |
| 6,071,291 A | 6/2000 | Forst et al. | |
| 6,087,553 A | 7/2000 | Cohen | |
| 6,093,188 A | 7/2000 | Murray | |
| 6,129,728 A | 10/2000 | Schumacher et al. | |
| 6,143,036 A | 11/2000 | Comfort | |
| 6,221,075 B1 | 4/2001 | Tormala et al. | |
| 6,238,214 B1 | 5/2001 | Robinson | |
| 6,315,798 B1 | 11/2001 | Ashby et al. | |
| 6,325,803 B1 | 12/2001 | Schumacher et al. | |
| 6,394,807 B2 | 5/2002 | Robinson | |
| 6,620,332 B2 | 9/2003 | Amrich | |
| 6,645,250 B2 | 11/2003 | Schulter | |
| 6,652,585 B2 | 11/2003 | Lange | |
| 6,692,497 B1 | 2/2004 | Tormala et al. | |
| 6,692,498 B1 | 2/2004 | Niiranen et al. | |
| 6,827,743 B2 | 12/2004 | Eisermann et al. | |
| 6,852,128 B2 | 2/2005 | Lange | |
| 2002/0050463 A1 | 5/2002 | McDowell | |
| 2002/0120348 A1* | 8/2002 | Melican et al. | 623/23.72 |
| 2002/0123750 A1 | 9/2002 | Eisermann | |
| 2003/0208205 A1 | 11/2003 | Gambale | |
| 2004/0054372 A1 | 3/2004 | Corden et al. | |
| 2004/0267349 A1 | 12/2004 | Richeter | |
| 2005/0043733 A1 | 2/2005 | Eisermann et al. | |
| 2005/0146070 A1 | 7/2005 | Muratoglu et al. | |
| 2005/0288790 A1 | 12/2005 | Swords | |
| 2006/0116682 A1 | 6/2006 | Longo | |
| 2006/0217813 A1 | 9/2006 | Posnick et al. | |
| 2006/0224242 A1 | 10/2006 | Swords | |
| 2007/0156146 A1 | 7/2007 | Metzger et al. | |
| 2009/0138067 A1 | 5/2009 | Pinchuk et al. | |

FOREIGN PATENT DOCUMENTS

| | | |
|---|---|---|
| DE | 2 404 214 | 1/1974 |
| EP | 0 092 260 A | 10/1983 |
| EP | 0 178 650 A2 | 4/1986 |
| EP | 0 423 420 A2 | 4/1991 |
| EP | 0 433 852 A1 | 6/1991 |
| EP | 0 544 384 A2 | 6/1993 |
| EP | 0 566 255 A1 | 10/1993 |
| EP | 0 654 250 A1 | 5/1995 |
| EP | 0 910 993 A2 | 4/1999 |
| GB | 2 059 267 A | 4/1981 |
| JP | 02237559 A | 9/1990 |
| JP | 9-173364 | 7/1997 |
| JP | 11155879 A | 6/1999 |
| WO | WO 97/41791 A | 11/1997 |
| WO | WO 99/37240 A | 7/1999 |
| WO | WO 02/092882 A1 | 11/2002 |
| WO | WO 03/084410 A1 | 10/2003 |
| WO | WO 2004/093743 A1 | 11/2004 |
| WO | WO-2007142743 A3 | 5/2008 |

OTHER PUBLICATIONS

Park, Hun K., Biomechanical properties of high-density polyethylene for pterional prosthesis, http://findarticles.com, Neurological Research, Oct. 2002.

Janecka, IP (2000): New reconstructive technologies in skull base surgery—Role of titanium mesh and porous polyethylene, Archives of Otolaryngology-head & Neck Surgery, 126 (3): 396-401 Mar. 2000.

Oka M., Ushio K., Kumar P., et al. (2000): Artifical Articular Cartilage, Proc Inst Mech Eng [H], 214(1):59-68,2000.

Murakami, N. Saito N., Horiuchi H., et al. (2002): Repair of segmental defects in rabbit humeri with titanium fiber mesh cylinders containing recombinant human bone morphogenetic protein-2 (rhBMP-2) and a synthetic polymer, J Biomed Mat Res, 62(2):169-174, Nov. 2002.

Murakami N., Saito N, Takahashi J., Ota H., et al. (2003): Repair of a proximal femoral bone defect in dogs using a porous surfaced prosthesis in combination with recombinant BMP-2 and a synthetic polymer carrier.

Liu, James K., M.D., et al., Porous Polyethylene Implant for Cranioplasty and Skull Base Reconstruction. Medscape, Apr. 12, 2004.

The Ahmed Glaucoma Valve, Ahmed website, 2004.

MEDPOR Biomaterials brochure, 05 pages, Porex Surgical, Inc. (2004).

Wong, 'Rigid mesh fixation for alloplastic cranioplasty,' J. Craniofac. Surg., 5(4):265-9 (1994) Abstract.

Guarda-Nardini, Use of porous plyethylene (Medpor) iin maxillofacial surgery, Minerva Stomatol., 44(12):559-82 (1995) Abstract.

Roberson, et al., 'Traumatic cranial defects reconstructed with the HTR-PMI cranioplastic implant,' J. Craniomaxillofac. Trauma, 3(2):8-13 (1997) Abstract.

Lara, et al., 'Technical considerations in the use of polymethylmethacrylate in cranioplasty,' J. Long Term Eff. Med. Implants, 8(1):43-53 (1998) Abstract.

Jones, et al., 'Combined use of titanium mesh and biocompatible osteoconductive polymer in the treatment of full thickness calvarial defects,' Br. J. Oral Maxillofac. Surg., 36(2):143-5 (1998) Abstract.

Temerkhanov, et al., 'The use of titanium mesh plates for graft fixation in mandibular osteoplasty,' Stomatologiia (Mosk), 77(6):31-3 (1998) Abstract.

Moe, et al., 'Resorbably fixation in facial plastic and head and neck reconstructive surgery: an initial report on polyactic acid implants,' Laryngoscope, 111(10):1697-701 (2001) Abstract.

Moualt, 'Acrylic cranioplasty and axial pattern flap following calvarial and cerebral mass excision in a dog,' Aust. Vet. J., 80(4):211-5 (2002) Abstract.

Supplementary Partial European Search Report from EP Appl. No. EP 04759969.1 issued May 2, 2008.

Marbacher, S. et al., Primary Reconstruction of Open Depressed Skull Fractures With Titanium Mesh; The Journal of Craniofacial Surgery, vol. 19, No. 2, Mar. 2008, pp. 490-495.

U.S. Appl. No. 11/445,560 Non-Final Office Action dated Oct. 29, 2008.

U.S. Appl. No. 11/445,560 Response to Office Action dated Dec. 23, 2008.

U.S. Appl. No. 11/445,560 Office Action dated May 9, 2008.

U.S. Appl. No. 11/445,560 Response to May 9, 2008 OA dated Jun. 2, 2008.

International Search Report for PCT/US07/009471 dated Aug. 8, 2008.

Janecka, I. P. "New Reconstructive Technologies in Skull Base Surgery", *Archieves of Otolaryngology Head and Neck Surgery* 2000, vol. 126, 396-401.

First Examination Report for EP04759969.1 issued by the European Patent Office on Sep. 29, 2008.

Office Action dated Nov. 12, 2009 issued in related U.S. Appl. No. 11/445,560.

U.S. Appl. No. 11/445,560 Second Non-Final Office Action dated Mar. 17, 2009.

* cited by examiner

CRANIOFACIAL IMPLANT

The applicant claims the benefit U.S. Application Nos. 60/463,036 and 60/496,684.

BACKGROUND OF THE INVENTION

Craniofacial and especially orbital wall and floor defects may result from trauma, cancer, resection, or congenital defects. Such defects are typically treated surgically using bone grafts or synthetic implants. Congenital defects or fractures of the complex and relatively thin bone structures surrounding and supporting the human eye present difficult internal bone repair and fixation problems. In instances when the eye is subject to trauma, the margin or rim of the orbit may diffuse the force of the impact. However, compression of the orbital contents sometimes may occur and fracture the relatively fragile orbit floor and/or the lateral and medial orbital walls. Also injury at the lateral orbital rim may produce a fracture within the orbit. When the orbit is fractured standard bone-grafting techniques for orbital reconstruction may not result in predictable eye function and positioning. Often the support of the globe is deficient as a result of under correction of the defect, over correction, or inadequate reconstruction of the orbital volume. Further, the bone graph may be subject to resorption that may result in result in a less than optimal support. The accurate anatomical reconstruction of the bony orbit is essential to maintain normal function and appearance of the eye following orbital fractures. Because most of the bone of the internal orbit surfaces is thin, it is difficult to adequately stabilize the fractured bone fragments without the use of autogenous or alloplastic materials.

Autologous bone grafts have been considered an optimal treatment method for orbital floor and wall reconstruction. However, this material is sometimes difficult to obtain and difficult to shape the bone graft material to properly fit within the orbit. There are problems relating to the tissue donor site morbidity. As discussed above, autogenous bone grafts have frequently been used by craniomaxillofacial surgeons for the reconstruction of the internal orbit. Bone may be harvested from the calvarium and other autogenous materials including iliac bone, split rib bone. Cartilage has also been used as a bone graft material. However, autogenous bones sometimes result in an unacceptable amount of resorption.

A variety of alloplastic materials have been used for orbital reconstruction and craniofacial applications including, silicone rubber, Teflon, Supramid, tantalum mesh, Vitallium mesh, titanium mesh, polyethylene, and methyl methacrylate Perforated biocompatible metallic strips and metallic panels may be used for rigid internal fixation of fractures in trauma surgery and as a plate material for bone immobilization and stabilization. Metal implants can be used for bone graft support material in reconstructive surgery.

Synthetic implant materials have the advantage of no donor site morbidity, ease of use, relative low cost and ready availability. While there are advantages of synthetic implants, some characteristics may be regarded as disadvantages. Silicone rubber has a smooth surface, but does not allow fibrovascular ingrowth into the implant. Further, although it is flexible, it does not readily conform to the profile of the region where it is required or maintain a new shape when shaped to fit a particular location. For example, in connection with the reconstruction of the orbit, a silicone rubber implant is not an attractive option because upon shaping it to the desired profile, it will tend to be biased back to its original shape. While a silicone rubber implant does not maintain its shape, in a case where the soft tissues of the orbit have been traumatized, an implant with a smooth superior surface is desirable to prevent attachment of the tissues to the implant upon healing. Attachment of these tissues to the wall of the implant may result in restriction of movement of the eye, causing diplopia, dizziness, and headaches, as well as a cosmetic anomaly on upgaze, downgaze or lateral gaze.

Implants having a porous structure such as porous polyethylene with predetermined pore sizes allow for fibrovascular ingrowth. In some circumstances fibrovascular ingrowth is desirable because it integrates the implant within the tissues, and reduces the possibility that that the synthetic material will be rejected. Further, fibrovascular ingrowth on the inferior or sinus side of the implant, allows for mucosalization of the implant surface, and, since the opposite side of the implant may be a barrier, the sinus is effectively isolated from the soft tissues of the orbit. This arrangement is considered desirable because it increases the ability of the implant to ward off infection and minimizes the chance of a sinus infection from entering through the orbit. Fibrovascular ingrowth is also thought to minimize the chance of implant migration or displacement. Porous polyethylene is somewhat flexible and thin sheets appropriate for orbital floor and wall reconstruction can be bent to an appropriate shape. However, this material tends to return to its original shape. Further, porous polyethylene does not have a smooth superior surface, so it may result in restriction of the orbital tissues due to fibrous ingrowth when used for orbital reconstruction.

Pure titanium is the material of choice in craniofacial reconstructive surgery, especially when the implant is intended to be permanent. As an implant material, pure titanium is preferred because its low density and elastic modules are less than some of the stainless steel or cobalt-chromium alloys that have been used as implant materials. Titanium is corrosion resistant and, when provided in thin sheets, is pliable. Titanium implants many be cut and shaped to the appropriate configuration at the time of surgery. Titanium mesh is easily moldable in situ and easily fixed to bone, but does not have smooth surfaces, nor does it allow for fibrovascular ingrowth. An easily molded material is desirable so that the surgeon can create the correct shape to properly reconstruct the orbital walls or orbital floor. Titanium mesh can be molded to the desired shape by hand and it will retain the shape due to the malleability and strength of the titanium material.

While there are a number of options for an implant material for orbital reconstruction, there remains a need for a material that is easily moldable by hand and will retain its shape after molding, has a smooth impenetrable surface on one side, and a porous surface on the opposite side, and is made from highly biocompatible materials. Preferably it is desirable to provide an implant that can be trimmed and bent to shape to fit the shape of the orbital wall or orbital floor reconstruction, and placed in the orbit with the smooth surface on the inside, against the periosteum and soft tissues and with the porous side directed toward the sinus region. Further, it would be desirable to provide a material that can be fixed to the orbital bones with surgical screws or to the surrounding tissues with sutures.

It is an object of the present invention to provide a unique implant for the repair of orbital defects and fixation of orbital fractures.

It is a further object of the invention to provide a unique composite implant structure which can be shaped for use during a surgical procedures relating to the repair of the orbit and be readily cut, reshaped or bent to conform to the orbital walls and affixed to the orbit or the orbital margin.

It is another object of the invention to provide an implant structure that forms a barrier between the sinus and the soft tissues of the orbit.

It is a further object of the invention to provide a craniofacial implant that may be used in other applications wherein it is desirable to maintain the shape of the implant.

Other objects and advantages of the invention will be apparent from the following summary and detailed description of the orbital repair implant structure of the invention taken with the accompanying drawing figures.

SUMMARY OF THE INVENTION

The present invention is directed to an improved implant and method of reconstruction of craniofacial defects, and in particular for orbital defects. The implant is a composite structure comprised of a surgical grade metal provided in a planar sheet form that is encased within a thermoplastic resin. In a first embodiment, one surface of the implant is smooth and impervious so that when the implant is placed within the body, it may form a barrier. In an alternative embodiment of the invention, while one side of the implant has a smooth surface, the opposite side of the implant is comprised of porous polyethylene that allows for fibrous tissue ingrowth. In a method of reconstruction, the implant that is described herein is cut and then shaped to conform to the profile of a defect to be treated. The implant is then secured to bony tissue using surgical screws or an alternative mechanical fastener. Because the implant contains a mesh it will maintain its shape.

DETAILED DESCRIPTION OF THE INVENTION AND THE PREFERRED EMBODIMENTS

The present invention is directed to novel implants for craniofacial surgery, methods for making said implant and a method of reconstructing orbital and cranial defects with the implants described. As described herein, a preferred application for the implant is for the reconstruction of orbital defects that may have resulted from trauma or disease or birth defects. Other craniofacial applications are also contemplated.

Figure 1:
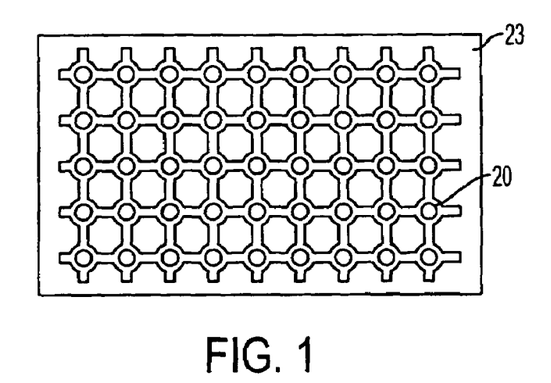
FIG. 1 is a top plan view of a first embodiment of an implant according to the invention wherein top side of the implant is a barrier surface.
Figure 2:
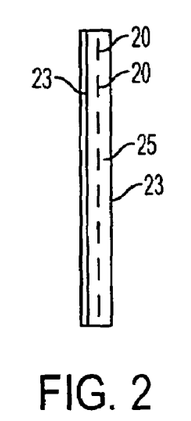
FIG. 2 is a side view in elevation of the first embodiment of the invention showing the barrier surface and the bottom porous surface.
Figure 3:
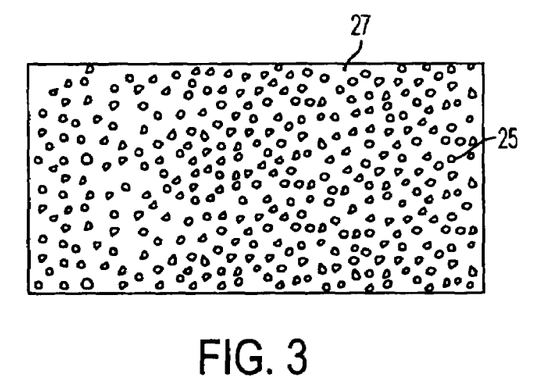
FIG. 3 is a bottom view of the first embodiment of the invention.

Now referring to FIG. 1, a first embodiment of the invention comprises a sheet of titanium mesh 20, with porous polyethylene formed in the interstices of the mesh and completely covering the bottom surface 27 of the implant. A solid sheet of polyethylene film 23 covers the top side of the implant. The mesh 20 provides for strength and serves to retain the shape of the implant in a rigid and fixed position. It should be understood that a mesh as used herein encompass any flat sheet of surgical grade metal that has perforations or passages formed through the sheet. The passages in the sheet help enable the sheet to be shaped or bent in more than one dimension and then retain the desired shape. It is contemplated that the mesh could be formed in a variety of manners including woven screens, or be etched from plates, or be formed from sold plates that are cut and then expanded to form a substrate having passages.

Figure 4:
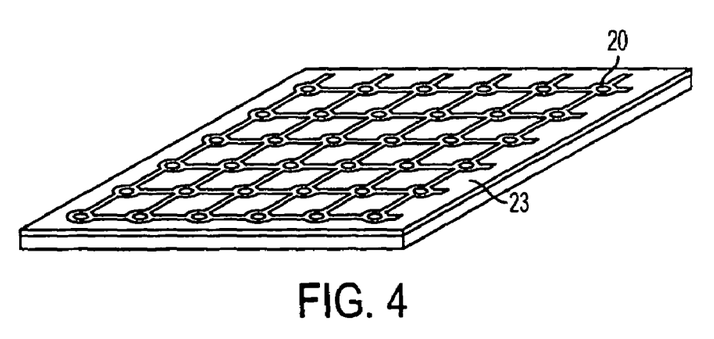
FIG. 4 is a perspective view of the first embodiment of the invention.

The first specific embodiment of the invention is illustrated in FIG. 1 where a smooth barrier material 23 lies on top of the titanium mesh material 20 with porous polyethylene 25 formed in the interstices and under the titanium mesh 20. As best seen in FIG. 4, the top surface 23 of the implant has some transparency so that the mesh 20 may be seen through the polyethylene film layer 23. While FIG. 1 shows the mesh 105 extended to the periphery of the implant, it is contemplated that in some embodiments the mesh may not extend to the edge of the implant structure. In yet other embodiments, the mesh may extend from the implant structure. In this later regard, it may be advantageous to extend the mesh from the implant structure to provide for a metal projection to be employed for the attachment of the implant during the surgical procedure. While in the embodiments depicted herein, the mesh is depicted in the center of the implant structure, it is contemplated that the mesh may be positioned adjacent to the top thin sheet layer or other locations within the implant depending on the respective application.

Figure 5:
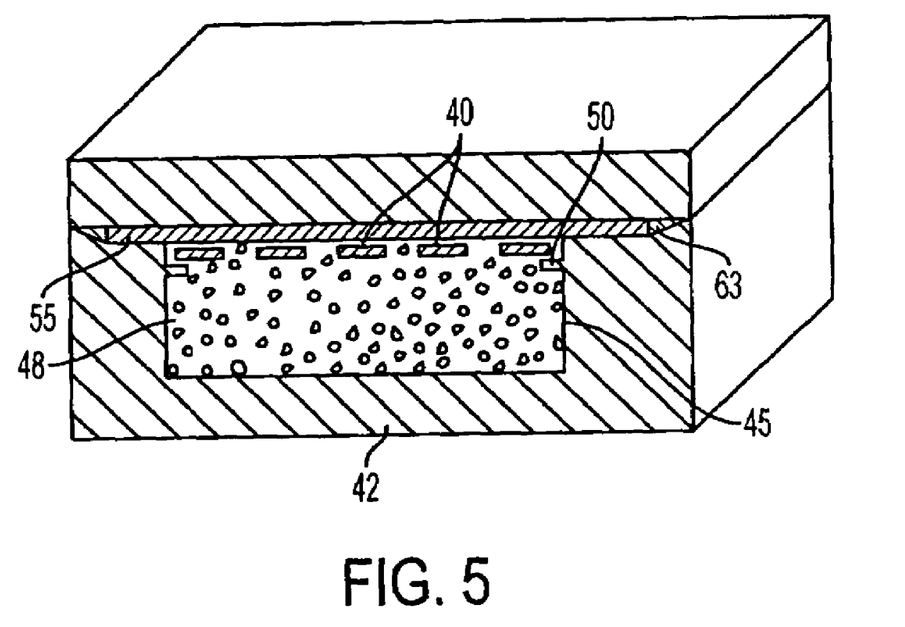
FIG. 5 is a side sectional view of an implant within a mold used to assemble the invention.

Now referring to FIG. 5, to manufacture the implant as depicted in FIG. 1, a mesh 40 is selected and positioned on tabs 50 that project form the sidewalls 45 and 48 of the bottom of the mold section 42. Next, polyethylene fines are introduced into the mold so that they fill the void below the mesh 40, the spaces between the titanium mesh 40 and cover the top surface of mesh 40. Last, a thin sheet or continuous film of solid polyethylene 55 is placed on the top of a suitable mold. The solid barrier sheet 55 extends beyond the edges of the cavity section of the mold and extends to the mold surface 63 thereby maintaining the sheet on one side of the mold.

Figure 7:
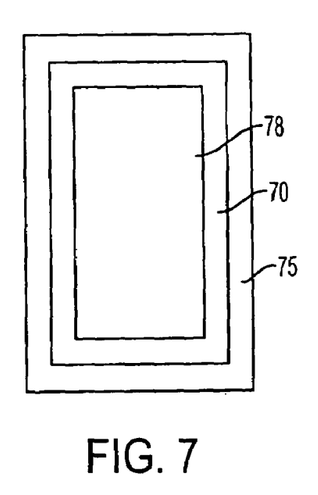
FIG. 7 is a top view of an alternative mold that can be used to create the invention with the top cover removed.
Figure 8:
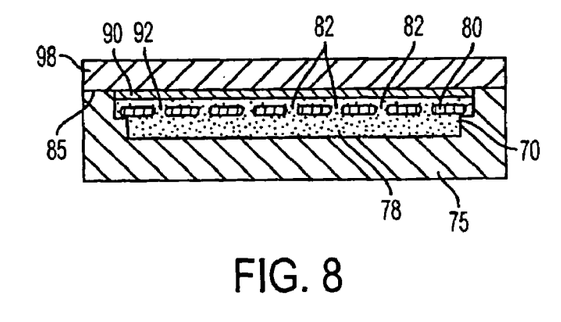
FIG. 8 is a side sectional view of the mold depicted in FIG. 7

FIG. 7 depicts an alternative arrangement for a mold wherein the mesh may be received on a shelf 70 that is suspended over the cavity using a shelf 70 around the mold cavity that holds the mesh sheet in position. As best seen in FIG. 8 shelf region 70 that extend into the void area 78 of mold 75 supports the edges of the mesh. A polyethylene sheet 90 is positioned above polyethylene fines 92 that fill the cavity 78. The passages through the mesh are identified by reference number 52. It should be understood that the dimensions, including the depth of the cavity from top surface 85 of bottom mold section 75, and the length and width of the mold may be altered depending on the particular application intended for the implant.

As illustrated by FIG. 8, the fines 92 come into contact with both the smooth polyethylene sheet 90 and the mesh 80. Once the mold is filled as described above, the top section 98 is placed over the components and the materials are subjected to heat and pressure, as is known in the current art, to form a porous polyethylene material. The heat and pressure causes the fines to be sintered together and to be affix the polyethylene sheet and titanium mesh. The resulting structure has titanium mesh embedded within a porous matrix and a solid smooth polyethylene film that is attached both to the titanium mesh and/or to the porous polyethylene structure. The sheet or film of polyethylene is impervious to water and serves as a barrier.

In a preferred embodiment of the invention described above, the polyethylene film is approximately 0.1 mm thick, the titanium mesh is approximately 0.35 mm thick, and the porous polyethylene is approximately 0.9 mm thick, inclusive of the embedded titanium mesh. Thus, the overall thickness of the material is approximately 1 mm.

Figure 13:
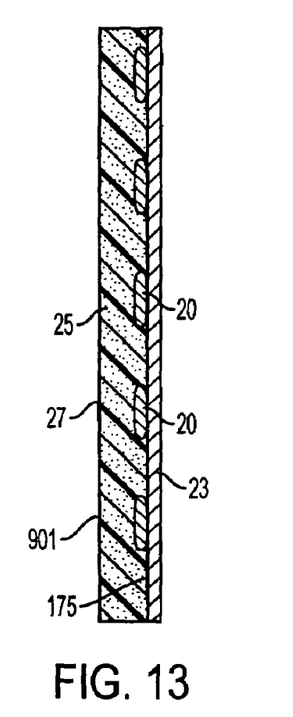
FIG. 13 is a side sectional view of the implant depicted in FIGS. 1-3.
Figure 14:
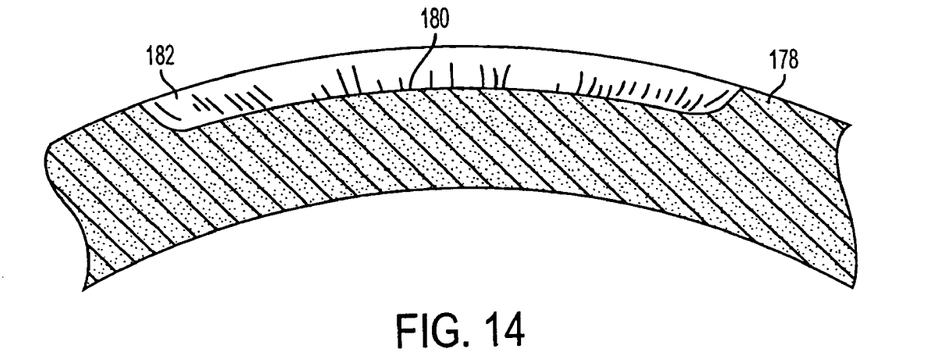
FIG. 14 depicts a sectional view of a cranial defect.
Figure 15:
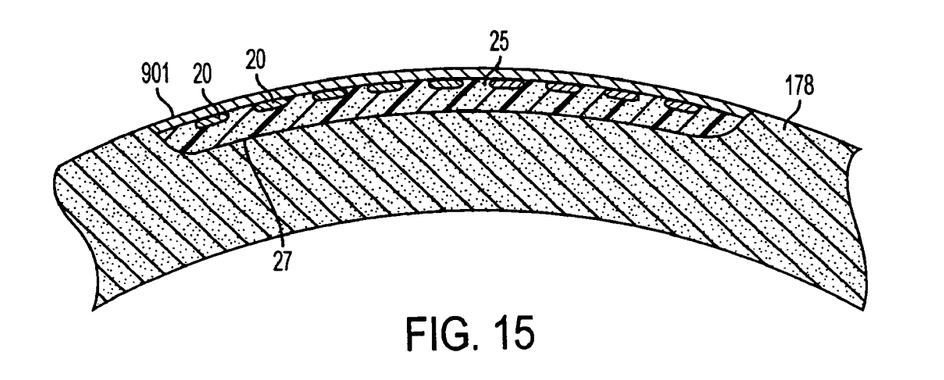
FIG. 15 is a side sectional view of the implant shown in FIGS. 1-3 within a cranial defect.

Now referring to FIG. 13, a side sectional view of the implant depicted in FIGS. 1-4 shows the mesh 20 formed along the interface 175 between the porous layer and the solid polyethylene layer 23. As seen in FIG. 14, a defect in the cranium 178 has a floor 180 and a wall 182. In order to address this defect, the implant is bent to confirm to the contour of the defect and cut to the shape of the defect. The implant is placed within the defect and the implant to the bone using appropriately sized surgical screws. In the preferred embodiment of the invention, the titanium is of sufficient strength in relation to the thickness of the polyethylene components (the solid sheet and the porous matrix) so that the implant will hold its shape after being bent by the surgeon. It is therefore contemplated that during a surgical procedure the surgeon may bend the implant to conform to the shape of the defect that is being treated. In a preferred embodiment the surgeon can bend the implant by hand during the procedure. The implant as described above can also be cut with conventional plate cutters that are routinely used for cutting titanium surgical plates or mesh.

Figure 9:
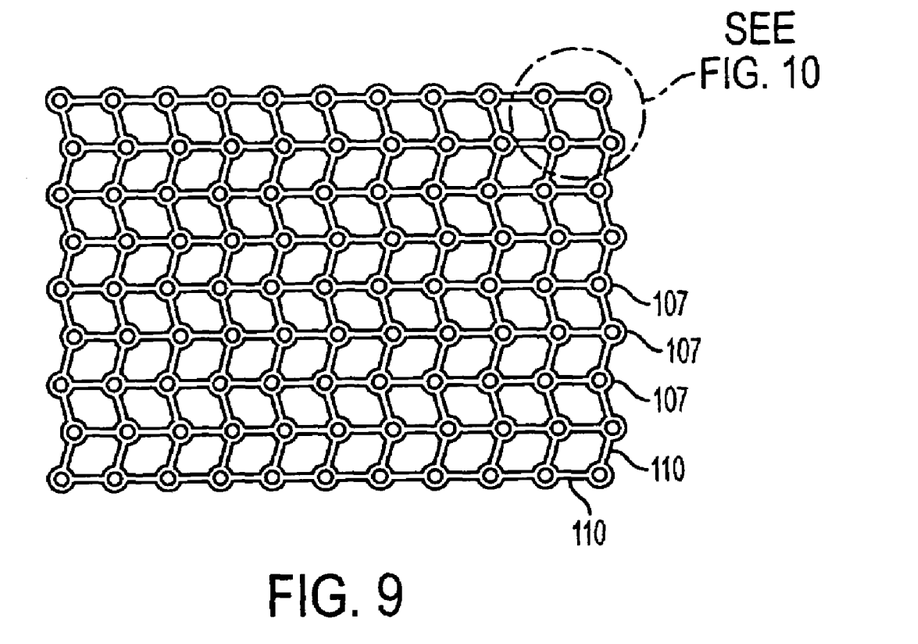
FIG. 9 is a top view of titanium mesh that may be employed with any of the embodiments of the invention.
Figure 10:
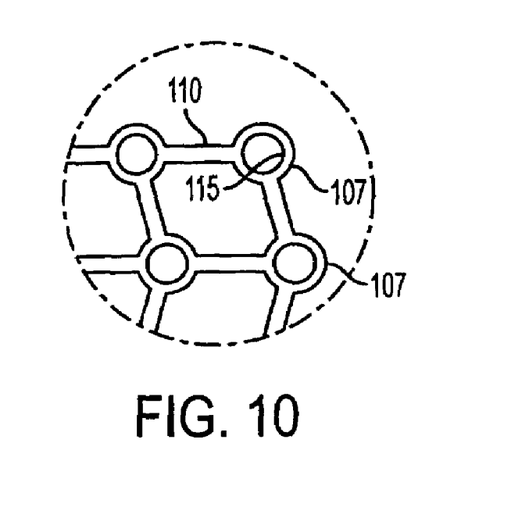
FIG. 10 is an enlarged view of a section of the titanium mesh depicted in FIG. 9.

While preferred embodiments of the titanium mesh are illustrated by FIGS. 9 and 10, other titanium mesh products that can be used in connection with the invention are commercially available from sources that include Stryker Instruments, Synthes Maxillofacial, Leibinger, KLS-Martin, L. P. and Walter-Lorenz Surgical.

Figure 11:
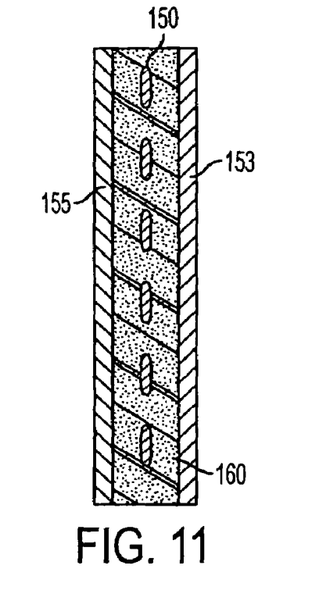
FIG. 11 is a side sectional view of an implant having opposite barrier surfaces that a center section.
Figure 12:
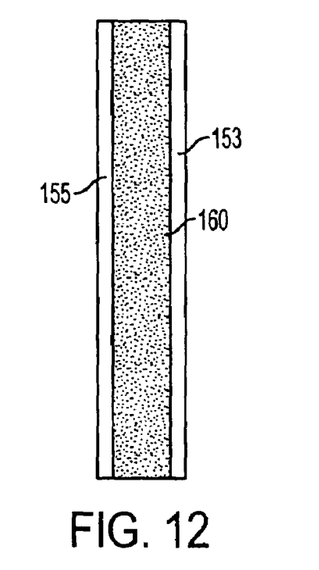
FIG. 12 is a side view in elevation of the implant depicted in FIG. 11.

FIG. 11 depicts yet another embodiment of the invention in which the titanium 150 is placed between two opposite polyethylene barrier sheets 153 and 155. A porous matrix 160 is sandwiched between the barrier sheets 153 and 155. use. The configuration of this implant provides a bendable sheet that has a smooth polyethylene surface on both the top and bottom surface. The implant will retain its shape after it has been bent to conform to the contours of defect to be treated. The implant has strength properties that are inherent to titanium, and it has a non-porous barrier surface that is not amenable to tissue attachment to the implant. The thickness of the sheets of polyethylene may be selected to result in an implant having the desired thickness. In the alternative, the thickness of the implant may be adjusted by variation of the porous matrix layer 160. Like the previous embodiments, the implant may be bent by the surgeon and it will maintain its shape.

Now referring to FIG. 13, a side sectional view of the implant depicted in FIGS. 1-4 shows the mesh 20 formed along the interface 175 between the porous layer and the solid polyethylene layer 23. As seen in FIG. 14, a defect in the cranium 178 has a floor 180 and a wall 182. In order to address this defect, the implant is bent to conform to the contour of the defect and cut to the shape of the defect. The implant is placed within the defect and the bottom porous layer is brought into contact with the bone on the floor and sidewalls. The implant may be secured into place with screws or sutures. Because the bottom surface and the sidewalls of the implant are porous, fibrovascular ingrowth into the implant is encouraged, and this ingrowth serves to further stabilize the implant and diminish the possibility of rejection. The smooth barrier surface prevents the dermis from attachment and thereby allows the skin to slide over the implant area.

Figure 18:
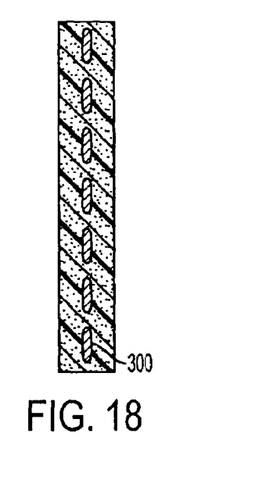
FIG. 18 is a side sectional view of a further embodiment of the invention wherein the metal mesh is formed with an implant with opposite porous surfaces.

In yet a further alternative embodiment of the invention, the structure involves the providing of a titanium mesh plate within a porous polyethylene matrix wherein all sides have porous surfaces. FIG. 18 depicts a sectional view wherein the mesh 300 is formed with a porous polyethylene matrix. This implant may be suitable for those applications where a smooth barrier surface is not indicated. For example, an implant having porous surfaces that allow for fibrovascular ingrowth on opposite sides may be indicated in cranial applications and for temporal implants for soft tissue replacement.

In the preferred embodiments of the invention described above, the pore size of the porous polyethylene is sized large enough to allow for fibrovascular ingrowth. This pore size range would preferably be in the range of 100-250 microns, but could vary in the range of 20-500 microns. While polyethylene sheets and high density porous polyethylene matrix are preferred, it is also contemplated that other synthetic resins and combinations can be used in connection with the invention. For example PETE, PTFE and/or nylon may be selected as the thermoplastic resin. It is also should be understood that the Figures depicted herein are not necessarily drawn to scale. For example, the barrier in FIGS. 1-4 may be formed with a sheet having a much smaller width than the drawings may suggest. In a preferred embodiment the invention as depicted in FIGS. 1-4 is approximately 5 mm wide by 10 mm in length and has a thickness of approximately 1 mm. However, other dimensions are contemplated.

FIG. 5 is a sectional view of the implant according to one embodiment of the invention located within a mold. As depicted therein, the mesh is located adjacent to the barrier layer on the top of the mold. The barrier layer is formed of a solid sheet of polyethylene, and the porous section is made by sintering together polyethylene fines under heat and pressure. The solid sheet may be made by introducing polyethylene fines to a press having opposite smooth metal sheets and heating the surfaces causing the fines to completely fuse together. When the implant has cooled, the structure may be removed from the mold because the tabs 50 and implant materials have some flexibility.

Figure 6:
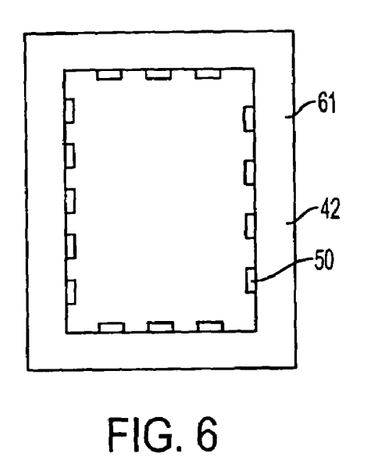
FIG. 6. is a top view of a mold depicted in FIG. 5 with the top cover removed.

Now referring to FIG. 6, a contemplated arrangement depicting a plurality of tabs 50 provided on the lower section of mold 61 is shown. The titanium sheet will rest on or is supported by the tabs 50 provided around the periphery of the mold. The tabs are placed a distance from the top surface of the mold that is slightly less than the width of the mesh, so that when the top of the mold that retains the barrier sheet is placed over the mold bottom, the thin barrier sheet may come into contact with the mesh. FIG. 7 depicts an alternative arrangement wherein the mold is provided with a shelf to retain the titanium mesh in position near the top of the mold.

Figure 16:
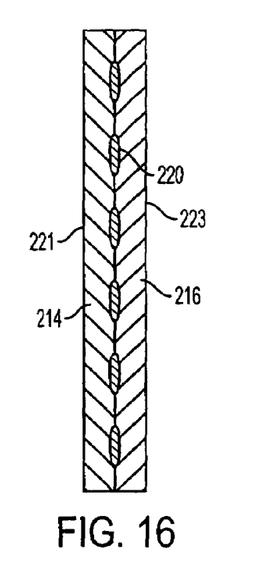
FIG. 16 is yet another embodiment of the invention wherein the implant has opposite barrier surfaces.
Figure 17:
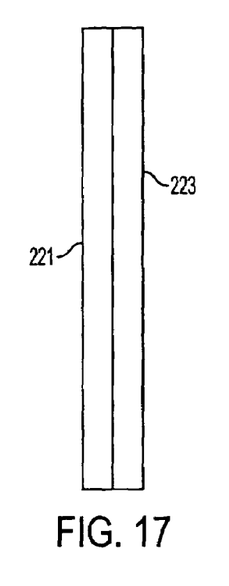
FIG. 17 is a side view in elevation of the implant depicted in FIG. 16.

FIG. 16 depicts yet a further embodiment of the implant wherein the top surface 214 and bottom surface 126 are polyethylene sheets. The mesh 220 is contiguous with the internal surfaces of both the top sheet 214 and the lower sheet 216. This implant has a top barrier surface 221 and bottom barrier surface 223 and is indicated in those applications where fibrovascular ingrowth is not desired.

Figure 19:
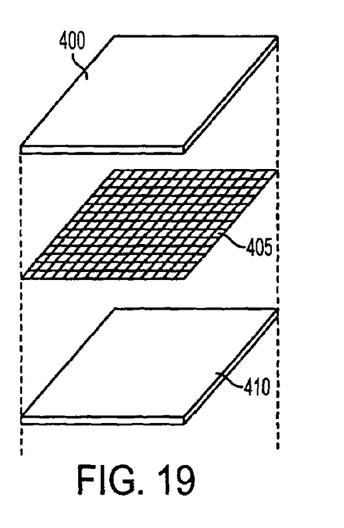
FIG. 19 is an exploded view of an implant having three layers.

FIG. 19 shows an exploded perspective schematic view of the embodiment according to the invention. Top layer 400 may comprise a barrier surface or porous surface. The mesh 405 may be any metallic material suitable for surgical applications that and that is malleable and will retain its shape. Bottom layer 410 may be a barrier surface or a porous surface. This embodiment depicts mesh 405 at the interface between the layers 400 and 410.

Figure 20:
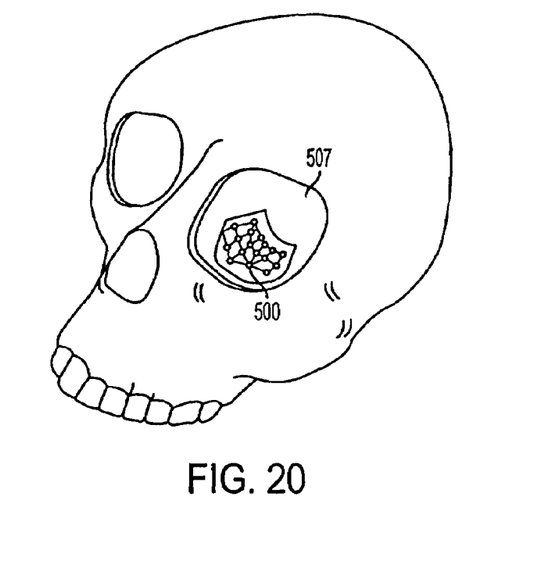
FIG. 20 is a perspective illustration of an implant according to the invention shown in an orbital reconstruction application.

FIG. 20 depicts an implant 500 made according to the invention in position on the orbit floor of an orbit 507. In addition to the repair and reconstruction of orbital defects, the implants according to the invention may be advantageously employed with other surgery such as the repair of lost bone flaps resulting from neurological procedures, repair of the mastoid area after a mastoidectomy, fixation for LeFort procedures, fixation for sliding genioplasty. It is further contemplated that the planar sheets may be bent into tubular shapes and used for orthopedic applications. A planar sheet bent in a U shaped configuration may be useful in connection with spinal fixation procedures or the repair of herniated disks.

The invention having been described in detail with respect to preferred embodiments above, it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

I claim:

1. A craniofacial implant comprising a porous polyethylene matrix and a surgical grade metal mesh embedded within the matrix such that the porous polyethylene matrix fills spaces within the mesh and encases the mesh such that all sides of the porous polyethylene matrix forming surfaces of the implant have pores that are sized between 20-500 microns, and wherein the implant is able to be bent or displaced by manipulation by hand such that the implant will generally maintain the shape to which it has been bent or displaced in a rigid and fixed position for attachment to bone, wherein the mesh provides a structure for attachment to bone.

2. The implant recited in claim 1, wherein the polyethylene matrix is porous throughout the implant.

3. The implant of claim 1, further comprising a structure for attachment to bone extending from the porous polyethylene matrix.

4. The implant of claim 3, wherein the structure for attachment to bone comprises a portion of mesh that extends beyond the encased mesh and the porous polyethylene matrix and is adapted to receive a surgical screw or surgical bone anchor.

5. The implant of claim 1, wherein the surgical grade metal mesh comprises titanium.

6. The implant of claim 1, wherein the porous polyethylene matrix comprises a high density polyethylene.

7. A craniofacial implant having a first surface and a second surface, the implant comprising a porous polyethylene matrix and a surgical grade metal mesh embedded within the matrix such that the porous polyethylene matrix fills spaces within the mesh and encases the mesh such that the second surface and sides of the porous polyethylene matrix have pores that are sized between 20-500 microns, wherein the first surface comprises a non-porous barrier surface of polyethylene, and wherein the implant is able to be bent or displaced by manipulation by hand such that the implant will generally maintain the shape to which it has been bent or displaced in a rigid and fixed position for attachment to bone, wherein the mesh provides a structure for attachment to bone.

8. The implant of claim 7, wherein the polyethylene matrix is porous throughout the matrix, and wherein the non-porous barrier surface of polyethylene is on the porous polyethylene matrix.

9. The implant of claim 7, further comprising a structure for attachment to bone extending from the porous polyethylene matrix.

10. The implant of claim 9, wherein the structure for attachment to bone comprises a portion of mesh that extends beyond the encased mesh and the porous polyethylene matrix and is adapted to receive a surgical screw or surgical bone anchor.

11. The implant of claim 7, wherein the surgical grade metal mesh comprises titanium.

12. The implant of claim 7, wherein the porous polyethylene matrix comprises a high density polyethylene.

* * * * *

UNITED STATES PATENT AND TRADEMARK OFFICE
CERTIFICATE OF CORRECTION

PATENT NO. : 7,655,047 B2  Page 1 of 1
APPLICATION NO. : 10/517843
DATED : February 2, 2010
INVENTOR(S) : Greg Swords It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 220 days.

Signed and Sealed this

Twenty-third Day of November, 2010

David J. Kappos
*Director of the United States Patent and Trademark Office*